United States Patent
Doisneau et al.

(10) Patent No.: US 10,604,613 B2
(45) Date of Patent: *Mar. 31, 2020

(54) HIGH-RIGIDITY RUBBER COMPOSITION

(71) Applicant: COMPAGNIE GENERALE DES ETABLISSEMENTS MICHELIN, Clermont-Ferrand (FR)

(72) Inventors: David Doisneau, Clermont-Ferrand (FR); Anne-Lise Thuilliez, Clermont-Ferrand (FR); Odile Gavard-Lonchay, Clermont-Ferrand (FR)

(73) Assignee: COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/545,138

(22) PCT Filed: Jan. 20, 2016

(86) PCT No.: PCT/EP2016/051051
§ 371 (c)(1),
(2) Date: Jul. 20, 2017

(87) PCT Pub. No.: WO2016/116468
PCT Pub. Date: Jul. 28, 2016

(65) Prior Publication Data
US 2017/0362370 A1 Dec. 21, 2017

(30) Foreign Application Priority Data
Jan. 21, 2015 (FR) ..................... 15 50456

(51) Int. Cl.
| | |
|---|---|
| *C08G 8/04* | (2006.01) |
| *C08L 7/00* | (2006.01) |
| *C08L 9/00* | (2006.01) |
| *C08L 61/12* | (2006.01) |
| *B60C 1/00* | (2006.01) |
| *C08G 8/06* | (2006.01) |
| *C08K 3/013* | (2018.01) |
| *C07C 39/10* | (2006.01) |
| *C07D 207/337* | (2006.01) |
| *C08J 3/00* | (2006.01) |
| *C08K 5/00* | (2006.01) |

(52) U.S. Cl.
CPC ................. *C08G 8/04* (2013.01); *B60C 1/00* (2013.01); *B60C 1/0041* (2013.01); *C07C 39/10* (2013.01); *C07D 207/337* (2013.01); *C08G 8/06* (2013.01); *C08J 3/005* (2013.01); *C08K 3/013* (2018.01); *C08K 5/0025* (2013.01); *C08L 7/00* (2013.01); *C08L 9/00* (2013.01); *C08L 61/12* (2013.01); *B60C 2001/0066* (2013.01); *C08L 2312/04* (2013.01)

(58) Field of Classification Search
CPC .............. C08G 8/02; C08G 8/04; C08L 61/12
See application file for complete search history.

(56) References Cited

U.S. PATENT DOCUMENTS

| | | | |
|---|---|---|---|
| 2,561,215 A | 7/1951 | Mighton | |
| 2,566,851 A | 9/1951 | Novotny et al. | |
| 2,902,470 A | 9/1959 | Kress | |
| 3,298,984 A * | 1/1967 | Rye .......................... | C08J 3/226 156/335 |
| 3,663,268 A * | 5/1972 | Wilson ...................... | C08J 5/06 156/335 |
| 3,817,778 A | 6/1974 | Wright | |
| 4,390,683 A | 6/1983 | Yatsu et al. | |
| 4,461,859 A | 7/1984 | Girgis | |
| 4,511,697 A | 4/1985 | Sohnemann | |
| 4,889,891 A * | 12/1989 | Durairaj ................. | C08G 16/02 156/335 |
| 5,030,692 A | 7/1991 | Durairaj ........................ | 525/134 |
| 5,202,390 A * | 4/1993 | Mulhaupt ................. | C08L 9/00 525/423 |
| 6,265,490 B1 * | 7/2001 | Morel-Fourrier ...... | C08G 61/02 525/149 |
| 7,199,175 B2 | 4/2007 | Vasseur | |
| 7,250,463 B2 | 7/2007 | Durel et al. | |
| 7,820,771 B2 | 10/2010 | Lapra et al. | |
| 7,900,667 B2 | 3/2011 | Vasseur | |
| 8,247,490 B1 * | 8/2012 | Li .......................... | C09J 109/02 524/510 |

(Continued)

FOREIGN PATENT DOCUMENTS

| | | |
|---|---|---|
| FR | 2485435 A1 | 12/1981 |
| FR | 2 489 830 A1 | 3/1982 |

(Continued)

OTHER PUBLICATIONS

"ASTM D412-06e2 Standard Test Methods for Vulcanized Rubber and Thermoplastic Elastomers—Tension", vol. D412, pp. 44-57 (2006).

(Continued)

*Primary Examiner* — Liam J Heincer
(74) *Attorney, Agent, or Firm* — Venable LLP

(57) ABSTRACT

A rubber composition comprises at least one phenol/aldehyde resin based on at least one aromatic polyphenol comprising at least one aromatic ring bearing at least two hydroxyl functions in the meta position relative to one another, the two positions ortho to at least one of the hydroxyl functions being unsubstituted, and at least one aldehyde of formula (A):

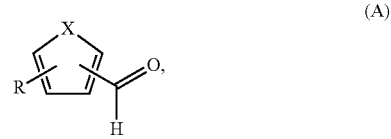

(A)

in which X comprises N, S or O, and R represents —H or —CHO.

14 Claims, 1 Drawing Sheet

(56) References Cited

U.S. PATENT DOCUMENTS

| | | | |
|---|---|---|---|
| 9,840,644 B2 * | 12/2017 | Doisneau | C09J 121/02 |
| 10,005,929 B2 * | 6/2018 | Doisneau | C09J 107/02 |
| 2003/0212185 A1 | 11/2003 | Vasseur | |
| 2004/0116592 A1 * | 6/2004 | Durairaj | C08L 7/00 |
| | | | 524/575.5 |
| 2004/0147712 A1 | 7/2004 | Durairaj et al. | |
| 2005/0004297 A1 | 1/2005 | Durel et al. | |
| 2007/0112120 A1 | 5/2007 | Vasseur | |
| 2008/0132644 A1 | 6/2008 | Lapra et al. | |
| 2009/0250151 A1 * | 10/2009 | Galimberti | B60C 1/00 |
| | | | 152/451 |
| 2009/0270558 A1 | 10/2009 | Gandon-pain et al. | |
| 2012/0000584 A1 | 1/2012 | Hahn et al. | |
| 2012/0101211 A1 | 4/2012 | Fujiki et al. | 524/511 |
| 2012/0211139 A1 | 8/2012 | Li | |
| 2012/0214372 A1 * | 8/2012 | Li | B29D 30/38 |
| | | | 442/59 |
| 2012/0214934 A1 * | 8/2012 | Li | C09J 109/02 |
| | | | 524/510 |
| 2012/0283372 A1 | 11/2012 | Veyland et al. | |
| 2013/0183483 A1 * | 7/2013 | Nair | F16F 9/0409 |
| | | | 428/114 |
| 2014/0216626 A1 * | 8/2014 | Peschek | B60C 9/11 |
| | | | 152/548 |
| 2014/0235124 A1 * | 8/2014 | Doisneau | C09J 121/02 |
| | | | 442/149 |
| 2014/0235125 A1 * | 8/2014 | Doisneau | C09J 107/02 |
| | | | 442/149 |
| 2014/0308864 A1 * | 10/2014 | Doisneau | C09J 107/02 |
| | | | 442/149 |
| 2015/0083297 A1 * | 3/2015 | Inata | C08L 61/12 |
| | | | 152/450 |
| 2016/0024353 A1 * | 1/2016 | Doisneau | C08G 4/00 |
| | | | 428/512 |
| 2016/0251550 A1 * | 9/2016 | Michoud | B60C 9/0042 |
| | | | 428/221 |
| 2016/0355631 A1 * | 12/2016 | Xu | C08J 3/24 |
| 2017/0165942 A1 * | 6/2017 | Michoud | B60C 9/0007 |
| 2017/0166010 A1 * | 6/2017 | Michoud | B32B 7/12 |
| 2018/0009972 A1 * | 1/2018 | Doisneau | B60C 1/00 |
| 2018/0016433 A1 * | 1/2018 | Doisneau | B60C 1/00 |
| 2019/0077952 A1 | 3/2019 | Thuilliez et al. | |

FOREIGN PATENT DOCUMENTS

| | | | |
|---|---|---|---|
| WO | 97/36724 A2 | 10/1997 | |
| WO | 99/16600 A1 | 4/1999 | |
| WO | 02/10269 A2 | 2/2002 | |
| WO | 03/016387 A1 | 2/2003 | |
| WO | 2005/042278 A2 | 5/2005 | |
| WO | 2006/069792 A1 | 7/2006 | |
| WO | 2006/069793 A1 | 7/2006 | |
| WO | 2013/017421 A1 | 2/2013 | |
| WO | WO-2013017422 A1 * | 2/2013 | C09J 107/02 |
| WO | WO-2013017423 A1 * | 2/2013 | C09J 107/02 |
| WO | 2014/111440 A2 | 7/2014 | |
| WO | 2015/000836 A1 | 1/2015 | |
| WO | 2015/007642 A1 | 1/2015 | |
| WO | 2015/118042 A1 | 8/2015 | |

OTHER PUBLICATIONS

International Search Report dated Mar. 14, 2016, issued by EPO in connection with International Application No. PCT/EP2016/051051.

* cited by examiner

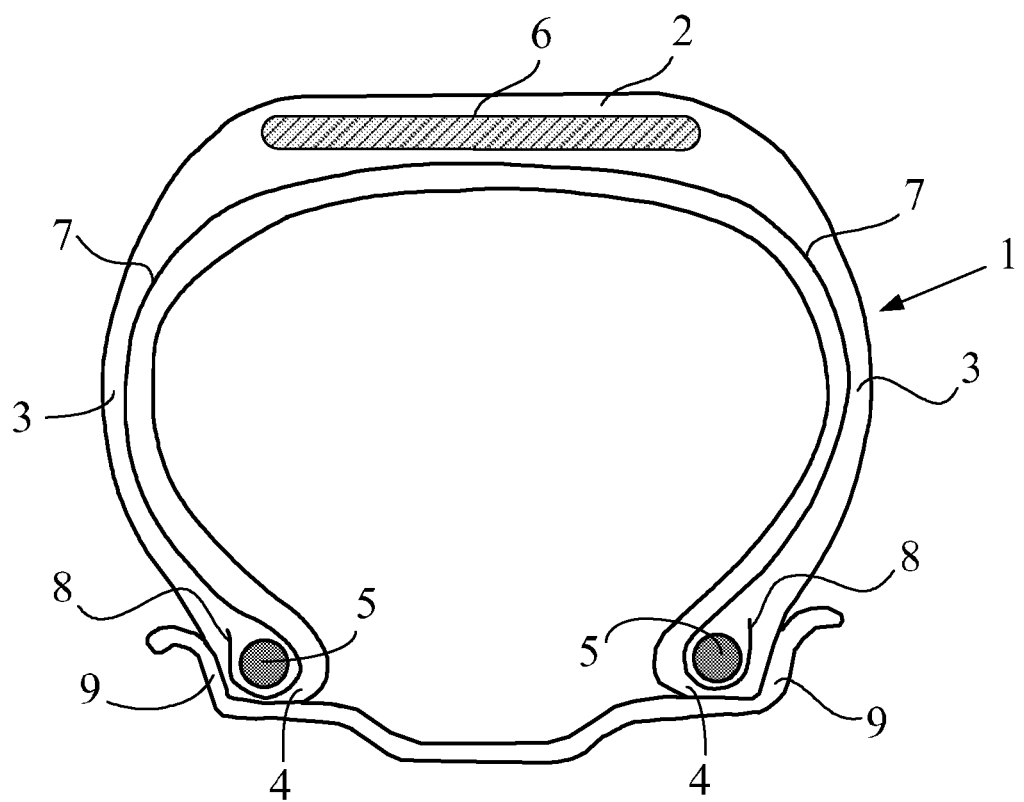

HIGH-RIGIDITY RUBBER COMPOSITION

FIELD OF THE INVENTION

The invention relates to a rubber composition, a method for manufacturing this composition, a rubber composite and a tyre.

RELATED ART

It is known to use, in some parts of the tyres, rubber compositions having high stiffness during small strains of the tyre. Resistance to small strains is one of the properties which a tyre must have in order to respond to the stresses to which it is subjected.

High stiffness may be obtained using what is referred to as a concentrated vulcanization system, that is to say especially comprising relatively high contents of sulphur and of vulcanization accelerator.

Nonetheless, such a concentrated vulcanization system detrimentally affects the uncured ageing of the composition. Thus, when the composition is in the form of a semi-finished product, for example of a rubber strip, the sulphur may migrate to the surface of the semi-finished product. This phenomenon, referred to as blooming, leads to a detrimental effect on the green tack of the semi-finished product during prolonged storage thereof, with, as consequence, degradation of the adhesion between the semi-finished products during manufacture of the tyre.

Moreover, storage of the uncured composition containing a concentrated vulcanization system is liable to lead to a reduction in the phase delay of the composition during vulcanization thereof, that is to say the time preceding the start of vulcanization. Consequently, the composition may begin to cure prematurely in certain forming tools and the vulcanization kinetics is liable to be altered and the vulcanization efficiency to be reduced.

Such a concentrated vulcanization system also detrimentally affects ageing in the cured state. Indeed, degradation of the mechanical properties of the cured composition is observed, especially at the limits, for example of the elongation at break.

High stiffness may otherwise be obtained by increasing the content of reinforcing filler.

Nonetheless, in a known way, increasing the stiffness of a rubber composition by increasing the content of filler may detrimentally affect the hysteresis properties and thus the rolling resistance properties of tyres. However, it is an ongoing aim to lower the rolling resistance of tyres in order to reduce the consumption of fuel and thus to conserve the environment.

Finally, high stiffness may be obtained by incorporating certain reinforcing resins, as disclosed in WO 02/10269.

Conventionally, the increase in stiffness is obtained by incorporating reinforcing resins based on a methylene acceptor/donor system. The terms "methylene acceptor" and "methylene donor" are well known to those skilled in the art and are widely used to denote compounds capable of reacting together to generate, by condensation, a three-dimensional reinforcing resin which will become superimposed and interpenetrated with the reinforcing filler/elastomer network, on the one hand, and with the elastomer/sulphur network, on the other hand (if the crosslinking agent is sulphur). The methylene acceptor is combined with a hardener, capable of crosslinking or curing it, also commonly known as "methylene donor". Examples of such methylene acceptors and donors are described in WO 02/10269.

The methylene donors conventionally used in rubber compositions for tyres are hexamethylenetetramine (abbreviated to HMT) or hexamethoxymethylmelamine (abbreviated to HMMM or H3M) or hexaethoxymethylmelamine.

The methylene acceptors conventionally used in rubber compositions for tyres are pre-condensed phenolic resins.

Nonetheless, the combination of phenolic resin conventionally used as methylene acceptor, with HMT or H3M as methylene donor, produces formaldehyde during the vulcanization of the rubber composition. However, it is desirable to reduce, or even eliminate in the long run, formaldehyde from rubber compositions due to the environmental impact of these compounds and the recent developments in regulations, especially European regulations, relating to this type of compound.

BRIEF DESCRIPTION OF EMBODIMENTS OF THE INVENTION

A subject of the invention is a rubber composition stiffened by means of compounds with low environmental impact, the stiffness being maintained in a range of high temperatures of use of the rubber composition, in particular for temperatures ranging up to 150° C.

To this end, a subject of the invention is a rubber composition comprising at least one phenol/aldehyde resin based on:

at least one aromatic polyphenol comprising at least one aromatic ring bearing at least two hydroxyl functions in the meta position relative to one another, the two positions ortho to at least one of the hydroxyl functions being unsubstituted, and at least one aldehyde of formula (A):

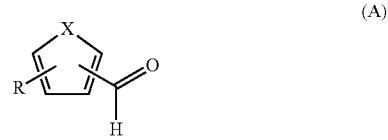

in which:
X comprises N, S or O,
R represents —H or —CHO.

Unexpectedly, the Applicants have discovered, during their research, that the aldehydes of formula (A) of the composition according to the invention make it possible to avoid the production of formaldehyde, unlike conventional methylene donors.

In addition, the specific combination of the aldehydes of formula (A) and of the aromatic polyphenols of the composition according to the invention makes it possible to obtain rubber compositions having a vastly improved stiffness at low strain compared to conventional rubber compositions which comprise the methylene donors HMT or H3M.

Moreover, the specific combination of the aldehydes of formula (A) and of the aromatic polyphenols of the composition according to the invention makes it possible to maintain high stiffness with increasing temperature.

Finally, such aldehydes result from renewable resources and not from oil. The aldehydes result, for example, from biobased resources or from products of the transformation of biobased sources.

The expression "resin based on" should, of course, be understood as meaning a resin comprising the mixture and/or the reaction product of the various base constituents used for this resin, preferably just the reaction product of the various base constituents used for this resin, it being possible for some of them to be intended to react, or capable of reacting, with one another or with their immediate chemical surroundings, at least partly, during the various phases of the method for manufacturing the composition, the composites or the tyre, in particular during a curing stage.

"Meta position relative to one another" is intended to mean that the hydroxyl functions are borne by carbons of the aromatic ring which are separated from one another by a single other carbon of the aromatic ring.

"Position ortho to a function" is intended to mean the position occupied by the carbon of the aromatic ring which is immediately adjacent to the carbon of the aromatic ring bearing the function.

The rubber composition thus comprises at least one (that is to say, one or more) crosslinked reinforcing resin, this reinforcing resin consisting of the phenol/aldehyde resin; this phenol/aldehyde resin being based on at least one (that is to say, one or more) aldehyde of formula (A) and at least one (that is to say, one or more) aromatic polyphenol, which constituents will be described in detail below.

Another subject of the invention is a method for manufacturing a rubber composition comprising a step of mixing:
at least one elastomer,
at least one aromatic polyphenol comprising at least one aromatic ring bearing at least two hydroxyl functions in the meta position relative to one another, the two positions ortho to at least one of the hydroxyl functions being unsubstituted, and
at least one aldehyde of formula (A):

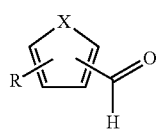

(A)

in which:
X comprises N, S or O,
R represents —H or —CHO.

Another subject of the invention is a rubber composite reinforced with at least one reinforcing element embedded in a rubber composition as described above.

Another subject of the invention is a tyre comprising a rubber composition as described above or a rubber composite as described above.

BRIEF DESCRIPTION OF DRAWING

The FIGURE diagrammatically shows a radial section of a tyre in accordance with the invention for a vehicle of the heavy-duty type.

DETAILED DESCRIPTION OF EMBODIMENTS OF THE INVENTION

Rubber composition is intended to mean that the composition comprises at least one elastomer or a rubber (the two terms being synonyms) and at least one other component. A rubber composition thus comprises a matrix of elastomer or of rubber in which at least the other component is dispersed. A rubber composition is in a plastic state in the uncured (non-crosslinked) state and in an elastic state in the cured (crosslinked) state, but never in a liquid state. A rubber composition must not be confused with an elastomer latex, which is a composition in a liquid state comprising a liquid solvent, generally water, and at least one elastomer or a rubber dispersed in the liquid solvent so as to form an emulsion. Thus, the rubber composition is not an aqueous adhesive composition.

In the present description, unless expressly indicated otherwise, all the percentages (%) shown are percentages by weight. The acronym "phr" signifies parts by weight per hundred parts of elastomer.

Furthermore, any range of values denoted by the expression "between a and b" represents the range of values extending from more than a to less than b (in other words excluding the limits a and b), whereas any range of values denoted by the expression "from a to b" means the range of values extending from the limit "a" as far as the limit "b", in other words including the strict limits "a" and "b".

Aromatic Polyphenol of the Rubber Composition

In a preferred embodiment, the aromatic ring of the aromatic polyphenol bears three hydroxyl functions in the meta position relative to one another.

The two positions ortho to each hydroxyl function are preferably unsubstituted. This is intended to mean that the two carbon atoms located on either side of (in the position ortho to) the hydroxylated carbon atom (i.e. that which bears the hydroxyl function) just bear a hydrogen atom.

Even more preferentially, the remainder of the aromatic ring of the aromatic polyphenol is unsubstituted. This is intended to mean that the other carbon atoms of the remainder of the aromatic ring (those other than the carbon atoms bearing hydroxyl functions) just bear a hydrogen atom.

In one embodiment, the aromatic polyphenol comprises several aromatic rings, at least two of these each bearing at least two hydroxyl functions in the meta position relative to one another, the two positions ortho to at least one of the hydroxyl functions of at least one aromatic ring being unsubstituted.

In a preferred embodiment, at least one of the aromatic rings of the aromatic polyphenol bears three hydroxyl functions in the meta position relative to one another.

The two positions ortho to each hydroxyl function of at least one aromatic ring are preferably unsubstituted.

Even more preferentially, the two positions ortho to each hydroxyl function of each aromatic ring are unsubstituted.

Advantageously, the, or each, aromatic ring of the aromatic polyphenol is a benzene ring.

Mention may in particular be made, as example of aromatic polyphenol comprising just one aromatic ring, of resorcinol and phloroglucinol, as a reminder of expanded formulae:

(I)

(II)

By way of examples, in the case in which the aromatic polyphenol comprises several aromatic rings, at least two of these aromatic rings, which are identical or different, are selected from those of general formulae:

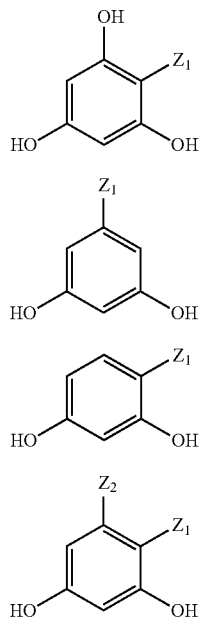

(III-a)

(III-b)

(III-c)

(III-d)

in which the $Z_1$ and $Z_2$ symbols, which are identical or different, if there are several of them on the same aromatic ring, represent an atom (for example, carbon, sulphur or oxygen) or a connecting group, by definition at least divalent, which connects at least these two aromatic rings to the remainder of the aromatic polyphenol molecule.

Another example of aromatic polyphenol is 2,2',4,4'-tetrahydroxydiphenyl sulphide of the following expanded formula:

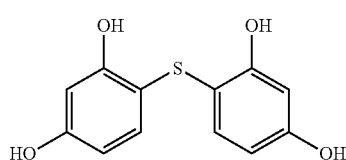

(IV)

Another example of aromatic polyphenol is 2,2',4,4'-tetrahydroxydiphenyl benzophenone of the following expanded formula:

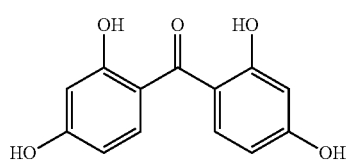

(V)

It is noted that each compound IV and V is an aromatic polyphenol comprising two aromatic rings (of formulae III-c), each of which bears at least two (in this instance two) hydroxyl functions in the meta position relative to one another.

It is noted, in the case of an aromatic polyphenol comprising at least one aromatic ring in accordance with formula III-b, that the two positions ortho to each hydroxyl function of at least one aromatic ring are unsubstituted. In the case of an aromatic polyphenol comprising several aromatic rings in accordance with formula III-b, the two positions ortho to each hydroxyl function of each aromatic ring are unsubstituted.

According to one embodiment of the invention, the aromatic polyphenol is selected from the group consisting of resorcinol (I), phloroglucinol (II), 2,2',4,4'-tetrahydroxydiphenyl sulphide (IV), 2,2',4,4'-tetrahydroxybenzophenone (V), resins pre-condensed from at least one of these phenols and the mixtures of these compounds. In a particularly advantageous embodiment, the aromatic polyphenol is phloroglucinol.

In the embodiment in which the aromatic polyphenol is a resin pre-condensed from at least one of these phenols, the resin preferably comprises a repeating unit, this unit comprising an aromatic ring bearing at least two hydroxyl functions in the meta position relative to one another. In the case in which this resin does not comprise a repeating unit, the resin comprises at least one aromatic ring bearing at least two hydroxyl functions in the meta position relative to one another.

Aldehyde of Formula A of the Rubber Composition

The aldehyde is preferentially of general formula (A'):

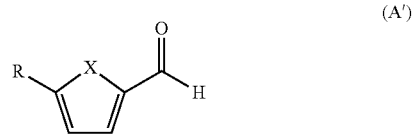

(A')

Even more preferentially, R represents —CHO.

According to a preferential embodiment, X represents O.

In a variant of the aldehyde of general formula (A), X represents O and R represents —H. The aldehyde used is then of formula (Ba):

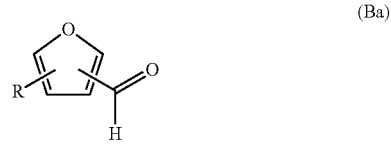

(Ba)

In a variant of the aldehyde of general formula (A'), X represents O and R represents —H. The aldehyde used is then furfuraldehyde and is of formula (B'a):

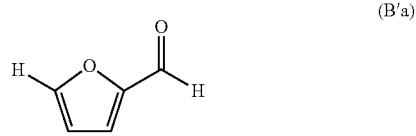

(B'a)

In another variant of the aldehyde of general formula (A), X represents O and R represents —CHO. The aldehyde used is then of formula (Bb):

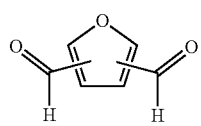
(Bb)

In another variant of the aldehyde of general formula (A'), X represents O and R represents —CHO. The aldehyde used is then 2,5-furandicarboxaldehyde and is of formula (B'b):

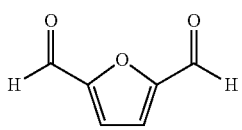
(B'b)

In another embodiment, X comprises N.

In an alternative form of the aldehyde of general formula (A), X represents NH. The aldehyde used is of formula (Ca):

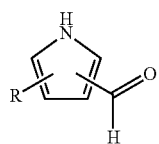
(Ca)

In a variant of the aldehyde of general formula (A'), X represents NH. The aldehyde used is of formula (C'a):

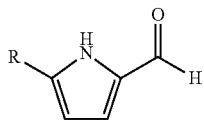
(C'a)

R preferably represents —CHO in the variant of the aldehyde of formula (C'a) and the aldehyde obtained is then 2,5-1H-pyrroledicarboxaldehyde.

In another variant of the aldehyde of general formula (A), X represents NR1 with R1 representing an alkyl, aryl, arylalkyl, alkylaryl or cycloalkyl group. The aldehyde used is of formula (Cb):

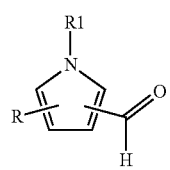
(Cb)

In another embodiment, X comprises S.

In a variant of the aldehyde of general formula (A), X represents S. The aldehyde used is of formula (Da):

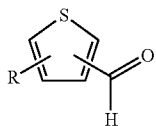
(Da)

In a variant of the aldehyde of general formula (A'), X represents S. The aldehyde used is of formula (D'a):

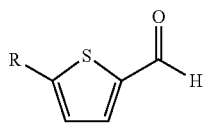
(D'a)

R preferably represents —CHO in the variant of the aldehyde of formula (IV'a) and is then 2,5-thiophenedicarboxaldehyde.

In another variant of the aldehyde of general formula (A), X represents SR2 with R2 representing an alkyl, aryl, arylalkyl, alkylaryl or cycloalkyl group. The aldehyde used is of formula (Db):

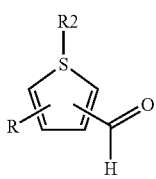
(Db)

In yet another variant of the aldehyde of general formula (A), X represents R3-S—R2 with R2 and R3 representing, each independently of one another, an alkyl, aryl, arylalkyl, alkylaryl or cycloalkyl group. The aldehyde used is of formula (Dc):

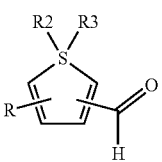
(Dc)

In yet another variant of the aldehyde of general formula (A), X represents S=O. The aldehyde used is of formula (Dd):

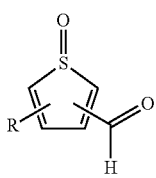
(Dd)

In yet another variant of the aldehyde of general formula (A), X represents O=S=O. The aldehyde used is of formula (De):

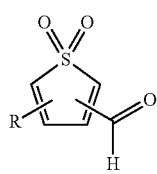

(De)

Among the different embodiments described above, preference will be given to the embodiments and variants in which X represents NH, S or O. In these embodiments and variants, it will be possible, in accordance with the invention, to have R representing —H or —CHO and preferably R representing —CHO. In these embodiments and variants, R will preferentially be in the 5 position and the —CHO group will preferentially be in the 2 position on the aromatic ring (general formula (A')).

The composition is preferably devoid of formaldehyde.

When the phenol/aldehyde resin is based on several aldehydes, at least one of which is an aldehyde of formula (A) in accordance with the invention, each aldehyde other than the aldehyde of formula (A) in accordance with the invention is preferentially different from formaldehyde. The composition is then also preferentially devoid of formaldehyde.

In other words and preferably, the or each aldehyde of the phenol/aldehyde resin is different from formaldehyde.

"Devoid of formaldehyde" is intended to mean that the content by weight of formaldehyde, by total weight of the aldehyde or aldehydes, is strictly less than 1%.

In some embodiments, the composition can comprise formaldehyde. Preferably, the composition then comprises a content by weight of formaldehyde, by total weight of the aldehyde or aldehydes, of less than or equal to 10%, preferably to 5% and more preferentially to 2%.

Rubber Composition

In some embodiments, an amount of aldehyde of formula (A) ranging from 0.1 to 30 phr will be used. Likewise, an amount of aromatic polyphenol ranging from 0.1 to 30 phr will be used.

In these embodiments, the rubber composition has a secant modulus at 10% elongation, MA10, measured according to standard ASTM D 412, 1998 (test specimen C) ranging from 5 to 25 MPa, preferably greater than or equal to 25 MPa. In particularly preferred embodiments, the MA10 is greater than or equal to 30 MPa, more preferentially greater than or equal to 35 MPs and even more preferentially strictly greater than 39 MPa.

The rubber composition preferably comprises a diene elastomer.

An elastomer or rubber (the two terms being synonyms) of the "diene" type is intended to mean, generally, an elastomer resulting at least in part (i.e., a homopolymer or a copolymer) from diene monomers (monomers bearing two conjugated or unconjugated carbon-carbon double bonds).

Particularly preferentially, the diene elastomer of the rubber composition is selected from the group consisting of polybutadienes (BRs), synthetic polyisoprenes (IRs), natural rubber (NR), butadiene copolymers, isoprene copolymers and the mixtures of these elastomers. Such copolymers are more preferentially selected from the group consisting of butadiene/styrene copolymers (SBRs), isoprene/butadiene copolymers (BIRs), isoprene/styrene copolymers (SIRs), isoprene/butadiene/styrene copolymers (SBIRs) and the mixtures of such copolymers.

The rubber compositions may contain just one diene elastomer or a mixture of several diene elastomers, it being possible for the diene elastomer or elastomers to be used in combination with any type of synthetic elastomer other than a diene elastomer, or even with polymers other than elastomers, for example thermoplastic polymers.

The rubber composition preferably comprises a reinforcing filler.

When a reinforcing filler is used, use may be made of any type of reinforcing filler known for its abilities to reinforce a rubber composition which can be used for the manufacture of tyres, for example an organic filler, such as carbon black, a reinforcing inorganic filler, such as silica, or else a blend of these two types of filler, especially a blend of carbon black and silica.

All the carbon blacks conventionally used in tyres ("tyre-grade" blacks) are suitable as carbon blacks. Mention will more particularly be made, for example, of the reinforcing carbon blacks of the 100, 200 or 300 series (ASTM grades).

In the case of the use of carbon blacks with an isoprene elastomer, the carbon blacks might, for example, be already incorporated in the isoprene elastomer in the form of a masterbatch (see, for example, applications WO 97/36724 or WO 99/16600).

Mention may be made, as examples of organic fillers other than carbon blacks, of functionalized polyvinylaromatic organic fillers, such as described in Applications WO-A-2006/069792 and WO-A-2006/069793.

"Reinforcing inorganic filler" should be understood, in the present application, by definition, as meaning any inorganic or mineral filler, regardless of its colour and its origin (natural or synthetic), also referred to as "white filler", "clear filler" or even "non-black filler", in contrast to carbon black, capable of reinforcing by itself alone, without means other than an intermediate coupling agent, a rubber composition intended for the manufacture of tyres, in other words capable of replacing, in its reinforcing role, a conventional tyre-grade carbon black. Such a filler is generally characterized, in a known way, by the presence of hydroxyl (—OH) groups at its surface.

The physical state in which the reinforcing inorganic filler is provided is not important, whether it is in the form of a powder, of microbeads, of granules, of beads or any other appropriate densified form. Of course, reinforcing inorganic filler is also intended to mean mixtures of different reinforcing inorganic fillers, in particular of highly dispersible siliceous and/or aluminous fillers as described below.

Mineral fillers of the siliceous type, in particular silica ($SiO_2$), or of the aluminous type, in particular alumina ($Al_2O_3$), are especially suitable as reinforcing inorganic fillers. The silica used may be any reinforcing silica known to those skilled in the art, especially any precipitated or fumed silica having a BET surface area and a CTAB specific surface area both of less than 450 $m^2/g$, preferably from 30 to 400 $m^2/g$. Mention will be made, as highly dispersible precipitated silicas ("HDSs"), for example, of the Ultrasil 7000 and Ultrasil 7005 silicas from Evonik, the Zeosil 1165MP, 1135MP and 1115MP silicas from Rhodia, the Hi-Sil EZ150G silica from PPG, the Zeopol 8715, 8745 and 8755 silicas from Huber or the silicas with a high specific surface area as described in Application WO 03/16837.

Finally, those skilled in the art will understand that, as filler equivalent to the reinforcing inorganic filler described in the present section, use might be made of a reinforcing filler of another, especially organic, nature, provided that this reinforcing filler is covered with an inorganic layer, such as silica, or else comprises functional sites, especially hydroxyl sites, at its surface which require the use of a coupling agent in order to establish the bond between the filler and the elastomer.

The content of total reinforcing filler (carbon black and/or reinforcing inorganic filler, such as silica) is preferably within a range extending from 5 to 120 phr, more preferentially from 5 to 100 phr and even more preferentially from 5 to 90 phr.

The content of total reinforcing filler is preferentially within a range extending from 10 to 120 phr, more preferentially from 10 to 100 phr and even more preferentially from 10 to 90 phr.

The content of total reinforcing filler is more preferentially within a range extending from 20 to 120 phr, more preferentially from 20 to 100 phr and even more preferentially from 20 to 90 phr.

The content of total reinforcing filler is even more preferentially within a range extending from 30 to 120 phr, more preferentially from 30 to 100 phr and even more preferentially from 30 to 90 phr.

The carbon black can advantageously constitute the sole reinforcing filler or the predominant reinforcing filler. Of course, it is possible to use just one carbon black or a blend of several carbon blacks of different ASTM grades. The carbon black can also be used as a blend with other reinforcing fillers and in particular reinforcing inorganic fillers as described above, in particular silica.

When an inorganic filler (for example silica) is used in the rubber composition, alone or as a blend with carbon black, its content is within a range from 0 to 70 phr, preferentially from 0 to 50 phr, in particular also from 5 to 70 phr, and even more preferentially this proportion varies from 5 to 50 phr, particularly from 5 to 40 phr.

The rubber composition preferably comprises various additives.

The rubber compositions may also comprise all or some of the standard additives customarily used in the elastomer compositions intended for the manufacture of tyres, such as for example plasticizers or extending oils, whether the latter are aromatic or non-aromatic in nature, pigments, protective agents, such as antiozone waxes, chemical antiozonants, antioxidants, antifatigue agents or else adhesion promoters.

The rubber composition preferably comprises a crosslinking system, more preferentially a vulcanization system.

The vulcanization system comprises a sulphur-donating agent, for example sulphur.

The vulcanization system preferably comprises vulcanization activators, such as zinc oxide and stearic acid.

The vulcanization system preferably comprises a vulcanization accelerator and/or a vulcanization retarder.

The sulphur or sulphur-donating agent is used at a preferential content within a range from 0.5 to 10 phr, more preferentially within a range from 0.5 to 8.0 phr. The combined vulcanization accelerators, retarders and activators are used at a preferential content within a range from 0.5 to 15 phr. The vulcanization activator or activators is or are used at a preferred content within a range from 0.5 to 12 phr.

The crosslinking system proper is preferentially based on sulphur and on a primary vulcanization accelerator, in particular on an accelerator of the sulphenamide type. Additional to this vulcanization system are various known secondary vulcanization accelerators or vulcanization activators, such as zinc oxide, stearic acid, guanidine derivatives (in particular diphenylguanidine), etc.

Use may be made, as (primary or secondary) accelerator, of any compound capable of acting as accelerator of the vulcanization of diene elastomers in the presence of sulphur, especially accelerators of the thiazole type and their derivatives and accelerators of the thiuram and zinc dithiocarbamate types. These accelerators are more preferentially selected from the group consisting of 2-mercaptobenzothiazole disulphide (abbreviated to "MBTS"), N-cyclohexyl-2-benzothiazolesulphenamide (abbreviated to "CBS"), N, N-dicyclohexyl2-benzothiazolesulphenamide (abbreviated to "DCBS"), N-(tert-butyl)-2-benzothiazolesulphenamide (abbreviated to "TBBS"), N-(tert-butyl)-2-benzothiazolesulphenimide (abbreviated to "TBSI"), zinc dibenzyldithiocarbamate (abbreviated to "ZBEC") and the mixtures of these compounds. Use is preferably made of a primary accelerator of the sulphenamide type.

The rubber composition may be in the uncured form, that is to say unvulcanized. The rubber composition may be in the cured form, that is to say vulcanized.

The rubber composition may preferably be used in the tyre in the form of a layer. Layer is intended to mean any three-dimensional element having any shape and any thickness, especially sheet, strip or other element having any cross section, for example rectangular or triangular.

Rubber Composition According to the Invention

The rubber composite is reinforced with at least one reinforcing element embedded in a rubber composition according to the invention.

This rubber composite can be prepared according to a process comprising at least the following steps:
  during a first step, combining at least one reinforcing element with a rubber composition (or elastomer; the two terms are synonymous) to form a rubber composite reinforced with the reinforcing element;
  then, during a second step, crosslinking by curing, for example by vulcanization, preferably under pressure, the composite formed in this way.

Among reinforcing elements, mention may be made of textile, metallic, or textile-metallic hybrid reinforcing elements.

"Textile" is intended to mean, in a way well known to those skilled in the art, any material made of a substance other than a metallic substance, whether natural or synthetic, which is capable of being transformed into thread or fibre by any appropriate transformation process. Mention may be made, for example, without the examples below being limiting, of a polymer spinning process, such as, for example, melt spinning, solution spinning or gel spinning.

This textile material may consist of a thread or fibre, or also of a fabric produced from threads or fibres, for example a woven fabric with warp threads and weft threads, or else a twill fabric with cross threads.

This textile material of the invention is preferably selected from the group consisting of monofilaments (or individual threads), multifilament fibres, assemblies of such threads or fibres, and mixtures of such materials. It is more particularly a monofilament, a multifilament fibre or a folded yarn.

The term thread or fibre is generally intended to mean any elongate element of great length relative to its cross section, regardless of the shape, for example circular, oblong, rectangular, square, or even flat, of this cross section, it being possible for this thread to be straight or not straight, for example twisted or wavy. The largest dimension of its cross section is preferentially less than 5 mm, more preferentially less than 3 mm.

This thread or fibre may take any known form. For example, it may be an individual monofilament of large diameter (for example and preferably equal to or greater than 50 µm), a multifilament fibre (consisting of a plurality of individual filaments of small diameter, typically less than 30 μm), a textile folded yarn or cord formed from several textile fibres or monofilaments twisted or cabled together, or else an assembly, group or row of threads or fibres, such as, for example, a band or strip comprising several of these monofilaments, fibres, folded yarns or cords grouped together, for example aligned along a main direction, whether straight or not.

The textile materials may be made of organic, polymeric or inorganic substances.

Mention will be made, as examples of inorganic substances, of glass or carbon.

The invention is preferentially implemented with materials made of polymeric substance, of both the thermoplastic and non-thermoplastic type.

Mention will be made, as examples of polymeric substances of the non-thermoplastic type, for example, of aramid (aromatic polyamide) and cellulose, both natural and artificial, such as cotton, rayon, flax or hemp.

Mention will preferentially be made, as examples of polymeric substances of the thermoplastic type, of aliphatic polyamides and of polyesters. Mention may especially be made, among the aliphatic polyamides, of the polyamides 4-6, 6, 6-6, 11 or 12. Mention may be made, among polyesters, for example of PET (polyethylene terephthalate), PEN (polyethylene naphthalate), PBT (polybutylene terephthalate), PBN (polybutylene naphthalate), PPT (polypropylene terephthalate), and PPN (polypropylene naphthalate).

By definition, metallic is intended to mean one or more threadlike elements made up predominantly (that is to say more than 50% of its weight) or entirely (100% of its weight) of a metallic material. The metallic material is preferably steel, more preferentially pearlitic (or ferritic-pearlitic) carbon steel advantageously comprising between 0.4% and 1.2% by weight of carbon.

The metallic reinforcing element may be a monofilament, a cord comprising several metallic monofilaments or a multistrand rope comprising several cords, then referred to as strands.

In the preferred case in which the reinforcing element comprises several metallic monofilaments or several strands, the metallic monofilaments or the strands are assembled by twisting or braiding. It is recalled that there are two possible techniques for assembly:

either by twisting: the metallic monofilaments or the strands undergo both a collective twist and an individual twist about their own axis, thereby generating an untwisting torque on each of the monofilaments or strands:

or by braiding: the metallic monofilaments or the strands only undergo a collective twist and do not undergo an individual twist about their own axis.

The reinforcing element optionally comprises several monofilaments and is of the rubberized in situ type, that is to say that the reinforcing element is rubberized from the inside, during the actual manufacture thereof, by a filling rubber. Such metallic threadlike elements are known to those skilled in the art. The composition of the filling rubber may be identical, or not identical, to the rubber composition in which the reinforcing element is embedded.

Each reinforcing element, when it is textile, is preferably coated with a layer of an adhesive composition or adhesive. The adhesive used is for example of the RFL (resorcinol-formaldehyde-latex) type or, for example, as described in the publications WO2013017421, WO2013017422, WO2013017423 or else WO2015007642. Thus, the rubber composition according to the invention is in direct contact with the adhesive composition. The adhesive composition is interposed between the rubber composition according to the invention and the reinforcing element.

Tyre According to the Invention

Such tyres are, for example, those intended to be fitted onto motor vehicles of the passenger type, SUVs ("Sport Utility Vehicles"), two-wheel vehicles (especially bicycles and motorcycles), aircraft, or industrial vehicles chosen from vans, "heavy-duty" vehicles—that is to say underground trains, buses, heavy road transport vehicles (lorries, tractors, trailers), off-road vehicles, such as agricultural or civil engineering machines—and other transport or handling vehicles.

By way of example, the single appended FIGURE represents very diagrammatically (without observing a specific scale) a radial section of a tyre in accordance with the invention for a vehicle of the heavy-duty type.

This tyre 1 comprises a crown 2 reinforced by a crown reinforcement or belt 6, two sidewalls 3 and two beads 4, each of these beads 4 being reinforced with a bead wire 5. The crown 2 is surmounted by a tread, not represented in this diagrammatic FIGURE. A carcass reinforcement 7 is wound around the two bead wires 5 in each bead 4, the turn-up 8 of this reinforcement 7 being, for example, positioned towards the outside of the tyre 1, which is here represented fitted onto its wheel rim 9. The carcass reinforcement 7 is, in a way known per se, composed of at least one ply reinforced by "radial" cords, for example made of metal, that is to say that these cords are positioned virtually parallel to one another and extend from one bead to the other so as to form an angle of between 80° and 90° with the median circumferential plane (plane perpendicular to the axis of rotation of the tyre which is located halfway between the two beads 4 and passes through the middle of the crown reinforcement 6).

This tyre 1 of the invention has, for example, the characteristic that at least a crown reinforcement 6 and/or its carcass reinforcement 7 comprises a rubber composition or a composite according to the invention. Of course, the invention relates to the objects described previously, namely the rubber composite and the tyre, both in the uncured state (before curing or vulcanization) and in the cured state (after curing).

Method According to the Invention

The manufacturing method described above and below makes it possible to manufacture the composition according to the invention.

The rubber composition may be manufactured in suitable mixers, using two successive preparation phases well known to those skilled in the art:

a first phase of thermomechanical working or kneading ("non-productive" phase) at high temperature, up to a maximum temperature of between 110° C. and 190° C., preferably between 130° C. and 180° C., followed by a second phase of mechanical working ("productive" phase) down to a lower temperature, typically of less than 110° C., for example between 40° C. and 100° C., during which finishing phase the crosslinking system is incorporated.

In one embodiment, the method comprises the following steps:

incorporating a reinforcing filler in a diene elastomer during a first ("non-productive") step, everything being kneaded thermomechanically (for example, once or several times), until a maximum temperature of between 110° C. and 190° C. is reached;

cooling the combined mixture to a temperature of less than 100° C.;

then incorporating, during a second ("productive") step, a crosslinking system, the aldehyde of formula (A) and the aromatic polyphenol;

kneading everything up to a maximum temperature of less than 110° C.

By way of example, the non-productive phase is carried out in a single thermomechanical step during which firstly all the necessary base constituents (a diene elastomer, reinforcing filler) are introduced into an appropriate mixer, such as a standard internal mixer, then secondly, for example after kneading for one to two minutes, the other additives, optional additional agents for covering the filler or optional additional processing aids, with the exception of the crosslinking system. The total kneading time, in this non-productive phase, is preferably between 1 and 15 min.

After cooling the mixture thus obtained, the crosslinking system, the aldehyde of formula (A) and the aromatic polyphenol are then incorporated in an external mixer, such as an open mill, maintained at a low temperature (for example between 40° C. and 100° C.). The combined mixture is then mixed (productive phase) for a few minutes, for example between 2 and 15 min.

The final composition thus obtained can subsequently be calendered, for example in the form of a sheet or of a slab, especially for laboratory characterization, or else extruded, for example in order to form a rubber profiled element used in the manufacture of a tyre.

Analogously to the composite according to the invention, the method for manufacturing the tyre comprises:

the step of manufacturing the composition described above, and a step of crosslinking this composition, for example by vulcanization, preferably under pressure, to form the tyre according to the invention.

The invention and its advantages will be easily understood in the light of the exemplary embodiments which follow.

Exemplary Embodiments of the Invention and Comparative Tests

These tests demonstrate that:

the stiffness of the rubber composition is vastly improved compared to a rubber composition using a conventional reinforcing resin based on a methylene acceptor with HMT or H3M as methylene donor, and the stiffness of the rubber composition is maintained at high temperatures, in particular for temperatures ranging up to 150° C.

In addition, the phenol/aldehyde resin of the composition according to the invention is devoid of formaldehyde and does not generate any formaldehyde during its formation.

For this purpose, several rubber compositions denoted hereinafter T0 to T14 and 15 were prepared as indicated above and are summarized in the appended table 1 below.

All the compositions T0 to T14 and 15 have the following portion in common in their formulations (expressed in phr, parts by weight per hundred parts of elastomer): 100 phr of natural rubber, 75 phr of carbon black N326, 1.5 phr of N-(1,3-dimethylbutyl)-N-phenyl-para-phenylenediamine, 1.5 phr of stearic acid, 5 phr of ZnO, 1 phr of N-(tert-butyl)-2-benzothiazolesulphamide and 2.5 phr insoluble sulphur 20H.

The composition T0 does not comprise any reinforcing resin added to this shared portion.

In addition to the shared portion, the composition T1 comprises a reinforcing resin based on hexamethylenetetramine (1.6 phr) and on a pre-condensed phenolic resin (4 phr). The composition T1 represents a conventional composition of the prior art, having greater stiffness than that of the composition T0.

In addition to the shared portion, each composition T2 to T7 comprises 14 phr of phenol and 14 phr of aldehyde, indicated in table 1.

In addition to the shared portion, each composition T8 to T14 comprises 14 phr of aromatic polyphenol and 14 phr of aromatic polyaldehyde, indicated in table 1.

In addition to the shared portion, the composition 15 comprises 14 phr of aromatic polyphenol and 14 phr of the aldehyde of formula (A), indicated in table 1.

The compositions T0 to T14 are not in accordance with the invention, unlike composition 15 which is in accordance with the invention.

The rubber composition 15 according to the invention comprises a phenol/aldehyde resin based on:

at least one aromatic polyphenol comprising at least one aromatic ring bearing at least two hydroxyl functions in the meta position relative to one another, the two positions ortho to at least one of the hydroxyl functions being unsubstituted, and at least one aldehyde of formula (A).

Each aromatic polyphenol of the resin of each composition T8 to T14 and 15 according to the invention is selected from the group consisting of resorcinol, phloroglucinol, 2,2',4,4'-tetrahydroxydiphenyl sulphide, 2,2',4,4'-tetrahydroxybenzophenone, resins pre-condensed from these phenols and the mixtures of these compounds.

Each aromatic polyphenol of each composition T8 and T9 comprises a single aromatic ring, in this instance a benzene ring, bearing two, and only two, hydroxyl functions in the meta position relative to one another. In the case in point, this is resorcinol.

Each polyphenol of each composition T10 and T11 and 15 according to the invention comprises a single aromatic ring, in this case a benzene ring, bearing three, and only three, hydroxyl functions in the meta position relative to one another. In the case in point, this is phloroglucinol.

For the aromatic polyphenols of each composition T8 to T11 and 15 according to the invention, the remainder of the aromatic ring of the aromatic polyphenol is unsubstituted. In particular, the two positions ortho to each hydroxyl function are unsubstituted.

Each aromatic polyphenol of each composition T12 to T14 comprises several aromatic rings, in this case benzene rings, at least two of these each bearing at least two hydroxyl functions in the meta position relative to one another. The two positions ortho to at least one of the hydroxyl functions of each aromatic ring are unsubstituted.

The aromatic polyphenol of the composition T14 is a resin pre-condensed from resorcinol and formaldehyde.

As a variant in the composition according to the invention, use may be made, as a replacement for the phloroglucinol, of an aromatic polyphenol comprising a single aromatic ring, for example a benzene ring, bearing two, and only two, hydroxyl functions in the meta position relative to one another. For example, resorcinol as in the compositions T8 and T9.

In another variant in the composition according to the invention, use may be made, as a replacement for the phloroglucinol, of an aromatic polyphenol comprising several aromatic rings, for example benzene rings, at least two of these each bearing at least two hydroxyl functions in the meta position relative to one another, as in the compositions T12 and T13. The two positions ortho to at least one of the hydroxyl functions of each aromatic ring are unsubstituted.

In yet another variant in the composition according to the invention, use may be made, as a replacement for the phloroglucinol, of an aromatic polyphenol comprising a resin pre-condensed from resorcinol and formaldehyde, as in the composition T14.

Each aromatic polyaldehyde of each composition T8 to T14 is either 1,3-benzenedicarboxaldehyde or 1,4-benzenedicarboxaldehyde. As a variant, this could be a mixture of 1,3-benzenedicarboxaldehyde and 1,4-benzenedicarboxaldehyde.

The aldehyde of formula (A of the composition 15 according to the invention is selected from the group consisting of furfuraldehyde, 2,5-furandicarboxaldehyde and the mixtures of these compounds. In this case, the aldehyde of formula (A) is 2,5-furandicarboxaldehyde.

The compositions T1 to T14 and 15 were prepared in accordance with the method described above, then the compositions were characterized by means of several characterization tests described below.

Firstly, the stiffness at high temperature was characterized, by heating the mixture to 150° C. until the maximum rheometric torque was obtained.

Once vulcanized, the stiffness at 23° C. of the composition was characterized during a tensile test.

Characterization of the Stiffness at High Temperature—Maximum Rheometric Torque

The measurements are carried out at 150° C. with an oscillating disc rheometer, according to Standard DIN 53529-Part 3 (June 1983). The change in the rheometric torque as a function of the time describes the change in the stiffening of the composition following vulcanization and crosslinking of the phenol/aldehyde resin. From the change in the rheometric torque, the maximum rheometric torque Cmax is determined, and reported in table 1. The higher the maximum rheometric torque Cmax, the more the composition has a stiffness which can be maintained at high temperature.

Characterization of the Stiffness at 23° C.—Tensile Test

These tests make it possible to determine the elasticity stresses and the properties at break. Unless indicated otherwise, they are carried out in accordance with standard ASTM D 412, 1998 (test specimen C). The "nominal" secant moduli (or apparent stresses, in MPa) at 10% elongation (denoted "MA10") are measured in second elongation (i.e., after an accommodation cycle). All these tensile measurements are carried out under normal temperature and relative humidity conditions, according to standard ASTM D 1349, 1999, and reported in table 1.

First of all, the results from table 1 show that the use of a reinforcing resin of the prior art (T1) makes it possible to obtain a stiffness at 23° C., and retention of this stiffness at higher temperatures, which are better than a composition devoid of reinforcing resin (T0). Nonetheless, despite better retention of the stiffness at high temperature than in compositions T2 to T7, the stiffness at 23° C. of the composition T1 is well below that of each composition T8 to T14 and 15 according to the invention.

Moreover, the results from table 1 show that the use of an aromatic monophenol (T2) does not make it possible to obtain sufficient stiffness at 23° C., nor retention of this stiffness at higher temperatures, unlike the aromatic polyphenols of the compositions T8 to T14 and 15 in accordance with the invention.

In addition, the results from table 1 show that the use of an aromatic aldehyde comprising a benzene ring bearing a single aldehyde function (T3 and T4) does not make it possible to obtain better stiffness at 23° C. compared to the composition T1, nor for this stiffness to be able to be maintained at higher temperatures, unlike the aldehyde of formula (A) of the composition 15. These results are relatively unexpected for those skilled in the art, given the fact that, a priori, the aldehyde of formula (A) of the composition 15 has lower reactivity than that of the aromatic monoaldehyde of the compositions T3 and T4.

The results from table 1 also show that while the use of 1,2-benzenedicarboxaldehyde (T5) makes it possible to obtain an improved stiffness at 23° C. compared to the composition T1, it does not make it possible to maintain this stiffness at high temperatures, unlike the aldehyde of formula (A) of the composition 15.

The use of an aromatic polyphenol, the two hydroxyl functions of which are in para positions (T6) relative to one another, does not make it possible to obtain an improved stiffness at 23° C. compared to the composition T1. Moreover, such a polyphenol does not enable the retention of this stiffness at higher temperatures.

Finally, the results from table 1 show that the use of an aromatic polyphenol, the two hydroxyl functions of which are in ortho positions (T7) relative to one another, does indeed make it possible to obtain an improved stiffness at 23° C. compared to the composition T1, without however enabling satisfactory retention of this stiffness at high temperatures, unlike the aromatic polyphenols in accordance with the invention (T8 to T14 and 15 in accordance with the invention).

The invention is not limited to the embodiments described above.

TABLE 1

| Composition | Methylene donor | Phenol | MA10 (MPa) | Cmax (dN·m) |
| --- | --- | --- | --- | --- |
| T0 | / | / | 7.2 | 16 |
| T1 | Hexamethylenetetramine (1) | SRF resin (2) | 16.5 | 43 |

| Composition | Aldehyde | Phenol | MA10 (MPa) | Cmax (dN·m) |
| --- | --- | --- | --- | --- |
| T2 | 1,4-benzenedicarboxaldehyde (5) | 3-tert-butylphenol (7) | 4.7 | 7 |
| T3 | Benzaldehyde (6) | Phloroglucinol (11) | 14.7 | 14 |
| T4 | Benzaldehyde (6) | Resorcinol (9) | 12.1 | 7 |
| T5 | 1,2-benzenedicarboxaldehyde (3) | Resorcinol (9) | 21.5 | 20 |
| T6 | 1,4-benzenedicarboxaldehyde (5) | Hydroquinone (10) | 13.6 | 7 |
| T7 | 1,4-benzenedicarboxaldehyde (5) | 1,2-dihydroxybenzene (8) | 36.2 | 25 |

| Composition | Aromatic polyaldehyde | Aromatic polyphenol | MA10 (MPa) | Cmax (dN·m) |
| --- | --- | --- | --- | --- |
| T8 | 1,3-benzenedicarboxaldehyde (4) | Resorcinol (9) | 28.7 | 30 |
| T9 | 1,4-benzenedicarboxaldehyde (5) | Resorcinol (9) | 32 | 73 |

TABLE 1-continued

| | Aldehyde | Polyphenol | MA10 (MPa) | Cmax (dN·m) |
|---|---|---|---|---|
| T10 | 1,3-benzenedicarboxaldehyde (4) | Phloroglucinol (11) | 39 | 35 |
| T11 | 1,4-benzenedicarboxaldehyde (5) | Phloroglucinol (11) | 33 | 30 |
| T12 | 1,4-benzenedicarboxaldehyde (5) | 2,2',4,4'-Tetrahydroxydiphenyl sulphide (12) | 32 | 45 |
| T13 | 1,4-benzenedicarboxaldehyde (5) | 2,2',4,4'-tetrahydroxybenzophenone (13) | 36.1 | 50 |
| T14 | 1,4-benzenedicarboxaldehyde (5) | SRF resin (2) | 35.1 | 50 |
| Composition | Aldehyde of formula (A) | Aromatic polyphenol | MA10 (MPa) | Cmax (dN·m) |
| 15 | 2,5-Furandicarboxaldehyde (14) | Phloroglucinol (11) | 25.7 | 40 |

(1) Hexamethylenetetramine (from Sigma-Aldrich; purity of ≥99%);
(2) Pre-condensed resin SRF 1524 (from Schenectady; diluted to 75%);
(3) 1,2-Benzenedicarboxaldehyde (from ABCR; purity of 98%);
(4) 1,3-Benzenedicarboxaldehyde (from ABCR; purity of 98%);
(5) 1,4-Benzenedicarboxaldehyde (from ABCR; purity of 98%);
(6) Benzaldehyde (from Sigma-Aldrich; purity of ≥99.5%);
(7) 3-Tert-butylphenol (from Sigma-Aldrich; purity of 99%);
(8) 1,2-Dihydroxybenzene (from Sigma-Aldrich; purity of 99%);
(9) Resorcinol (from Sumitomo; purity of 99.5%);
(10) Hydroquinone (from Sigma-Aldrich; purity of 99%);
(11) Phloroglucinol (from Alfa Aesar; purity of 99%);
(12) 2,2',4,4'-Tetrahydroxydiphenyl sulphide (from Alfa Aesar; purity of 98%);
(13) 2,2',4,4'-Tetrahydroxybenzophenone (from Sigma-Aldrich; purity of 97%);
(14) 2,5-Furandicarboxaldehyde (from Aldrich; purity of 97%).

The invention claimed is:

1. A method for manufacturing a solid rubber composition comprising the steps of:
incorporating, in a diene elastomer, during a first step, a reinforcing filler, to make a mixture and kneading the mixture thermomechanically until a maximum temperature of between 110° C. and 190° C. is reached; cooling the mixture to a temperature of less than 100° C.; then incorporating, during a second step, a crosslinking system, at least one aromatic polyphenol comprising at least one aromatic ring bearing at least two hydroxyl functions in the meta position relative to one another, the two positions ortho to at least one of the hydroxyl functions being unsubstituted, and at least one aldehyde of formula (A)

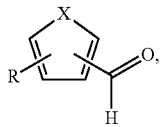

in which X comprises N, S or O, and R represents CHO; and kneading the mixture up to a maximum temperature of less than 110° C.,
wherein the rubber composition comprises from 30 to 90 phr total reinforcing filler.

2. The method according to claim 1, wherein the at least one aromatic ring bears three hydroxyl functions in the meta position relative to one another.

3. The method according to claim 1, wherein the two positions ortho to each hydroxyl function are unsubstituted.

4. The method according to claim 1, wherein the remainder of the at least one aromatic ring is unsubstituted.

5. The method according to claim 1, wherein the at least one aromatic polyphenol comprises several aromatic rings, at least two of these each bearing at least two hydroxyl functions in the meta position relative to one another, the two positions ortho to at least one of the hydroxyl functions of at least one aromatic ring being unsubstituted.

6. The method according to claim 1, wherein at least one of the aromatic rings of the at least one aromatic polyphenol bears three hydroxyl functions in the meta position relative to one another.

7. The method according to claim 1, wherein the two positions ortho to each hydroxyl function of at least one aromatic ring are unsubstituted.

8. The method according to claim 1, wherein the two positions ortho to each hydroxyl function of each aromatic ring are unsubstituted.

9. The method according to claim 1, wherein the at least one, or each, aromatic ring of the at least one aromatic polyphenol is a benzene ring.

10. The method according to claim 1, wherein the at least one aromatic polyphenol is selected from the group consisting of resorcinol, phloroglucinol, 2,2',4,4'-tetrahydroxydiphenyl sulphide, 2,2',4,4'-tetrahydroxybenzophenone, resins pre-condensed from at least one of these phenols, and mixtures thereof.

11. The method according to claim 1, wherein the at least one aldehyde is of general formula (A')

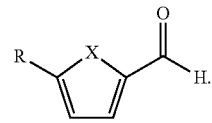

12. The method according to claim 1, wherein X represents NH, S or O.

13. The method according to claim 1, wherein the at least one aldehyde is 2,5-furandicarboxaldehyde.

14. The method according to claim 1 wherein the diene elastomer is selected from the group consisting of polybutadienes, synthetic polyisoprenes, natural rubber, butadiene copolymers, isoprene copolymers, and mixtures thereof.

* * * * *